US006617126B1

(12) United States Patent
Horn

(10) Patent No.: US 6,617,126 B1
(45) Date of Patent: Sep. 9, 2003

(54) METHOD FOR IMPROVING THE GROWTH AND COLORIMETRIC DETECTION OF BACTERIA, YEASTS, FUNGI OR COCCI

(75) Inventor: Jürgen Horn, Egelsbach (DE)

(73) Assignee: Biotest AG, Dreieich (DE)

(*) Notice: Subject to any disclaimer, the term of this patent is extended or adjusted under 35 U.S.C. 154(b) by 0 days.

(21) Appl. No.: 09/672,724

(22) Filed: Sep. 28, 2000

Related U.S. Application Data

(62) Division of application No. 08/889,927, filed on Jan. 8, 1997, now Pat. No. 6,168,930.

(30) Foreign Application Priority Data

Jan. 24, 1996 (DE) ........................................ 196 02 345

(51) Int. Cl.[7] .................................................. C12Q 1/04
(52) U.S. Cl. ......................................... 435/34; 435/244
(58) Field of Search ............................... 435/4, 34, 38, 435/39, 244, 253.6, 325

(56) References Cited

U.S. PATENT DOCUMENTS 5,096,718 A * 3/1992 Ayres et al. .................... 426/9
5,523,214 A * 6/1996 Horn ........................... 435/52
5,872,104 A * 2/1999 Vermeulen et al. ........... 514/29
6,136,554 A * 10/2000 Bochner ...................... 435/34
6,168,930 B1 * 1/2001 Horn ........................... 435/34

OTHER PUBLICATIONS

Merlin G. Precautions for Routine Use of INT Reductase Activity for Measuring Biological Activities in Soil and Sediments. Environmental Toxicology and Water Quality 10(3)185–192, Aug. 1995.*

Zwolska–Kwiek Z. The Usefulness of Tetrazole Salts for Testing the Reducing Ability of Bacilli. Gruzlica 42(1)75–83, 1974.*

O'Barr T. Comparative NADH Diaphorase Content of Isoniazid Resistant and Isoniazid Susceptible M. Tuberculosis. American Review of Respiratory Disease. 99(1)116–118, 1969.*

Tuovila B. Effect of Species Difference and Growth Rate in the Use of INT as an Indicator of Bacterial Respiration. J of Microbiological Methods 4(3–4)185–188, 1985.*

Edelstein P. Susceptibility of Legionella spp. to Mycinamicin I and II. Antimicrobial Agents and Chemotherapy 22(1)90–93, 1982.*

Bovill R. A. Comparison of the Fluorescent Redox Dye 5–cyano–2,3–ditolyltetrazolium Chloride With p–iodonitrotetrazolium Violet To Detect Metabolic Actvity In Heat Stressed Listeria monocytogenes Cells. J of Applied Bacteriology vol 77, pp. 353–358.*

Padhye A. Simple Method of Inducing Sporulation by Apophysomyces elegans and Saksenaea vasiformis. J of Clinical Microbiolgy 26(9)1861–1863, Sep. 1988.*

Edelstein P. Susceptibility of Legionella spp. to Mycinamicin I and II and Other Macrolide Antibiotics. Antimicrobial Agents and Chemotherapy 22(1)90–93. Jul. 1982.*

Wutzler P. Suitability of Peracetic Acid for Sterilization of Media for Mycoplasma Cultures. J of Clinical Microbiology 1(3)246–249. Mar. 1975.*

Sinha D. P. Observations on the In Vitro Cultivation of Hymenolepis nana. The Annals of Zoology 14(3)119–130. Jul. 1978.*

Sigma Catalog, pp. 983 and 567.

Sigma–Aldrich Handbook of Stains, Dyes and Indicators, 1990, Aldrich Chemical Co., pp. 410 and 717.

E. Barnes, J. Gen. Microbiol., 14: 57 (1956).

Manual of Clinical Microbiology, $7^{th}$ Edition, P. Murray, Editor, ASM Press, Washington, 1999, p. 399.

* cited by examiner

*Primary Examiner*—Ralph Gitomer
(74) *Attorney, Agent, or Firm*—Norris McLaughlin & Marcus

(57) ABSTRACT

The present invention relates to a method for improving the growth and detection of bacteria, yeasts, fungi or cocci, by adding sterile-filtered yeast extract and/or p-iodonitrotetrazolium violet to the culture medium.

11 Claims, No Drawings

METHOD FOR IMPROVING THE GROWTH AND COLORIMETRIC DETECTION OF BACTERIA, YEASTS, FUNGI OR COCCI

This application is a division of U.S. Ser. No. 08/889, 927, filed Jan. 8, 1997, now U.S. Pat. No. 6,168,930 which claims priority to German Application 196 02 345.9 filed Jan. 24, 1996.

The present invention relates to a method for improving the growth and the detection of bacteria, yeasts, fungi, or cocci, by adding to the culture medium sterile-filtered yeast extract and/or p-iodonitrotetrazolium violet.

The method is especially suited for the detection of mycobacteria or germs under stress conditions, such as airborne germs after the stress of desiccation in the air.

Special embodiments of the method of the invention are described hereinbelow.

The growth of bacteria, yeasts, fungi, cocci and germs is performed commonly on culture media known for the purpose. Their detection can then be performed by colorimetric methods using appropriate indicators.

For bacteria, cocci and other germs, nutrient mediums are generally used, such as tryptic soy agar or broth; yeasts and fungi can be cultured, for example, on Sabouraud agar, broth or RMPI 1640 broth. Common methods for mycobacteria are performed on a basis of egg or egg jelly, such as L öwenstein-Jensen or Stonebrinlk or agar media such as Middlebrook 7H10, 7H11, or fluid media such as Middlebrook 7H9 or Kirchner medium with 10% horse serum (DIN 58 943-3, Manual of Clinical Microbiology, 6th ed., 414–416).

For growth detection, the evaluation of $C^{14}$ palmitic acid can be used, which releases $^{14}CO_2$ (Bactec, Manual of Clinical Microbiology, 6th ed., 415); also oxygen consumption in the medium which is indicated by a fluorescent indicator (EP-A 0 509 781 Al, commercial name of the product MGIT) or by barometric measurement (ESP Automat für Blutkultur und Mykobalkterien, Difco) and by redox indicators such as resazurine/methylene blue (DE 4 316 394) or tetrazolium chloride (Deutsche Medizinische Wochenschrift 75, 1471 (1995)).

The growth of bacteria takes place relatively slowly. Mycobacteria on solid media require about 2–6 weeks, depending on the mycobacteria used for inoculation, and in liquid media 1–3 weeks. Growth detection with additional apparatus is very expensive, as is also the disposal of the radioactive waste. In known colorimetric redox indicators such as resazurine/methylene blue or tetrazolium chloride, the effect is seen that, for example, clinical strains of *Mycobacteria tuberculosis* are inhibited at low germ counts and do not grow satisfactorily except in high germ counts. However, even low germ counts have to be detected reliably in clinical test material. Furthermore, these indicators are toxic in the large amounts which are needed for low germ counts. Reducing the amount of these colorimetric redox indicators reduces the toxicity, but the result is that clinical isolates, such as those of *Mycobacterium tuberculosis*, do grow, but they are no longer colored, i.e., the desired colorimetric detection is not accomplished.

In the isolation and detection of airborne gents of various kinds, such as bacteria, cocci, yeasts, fungi and spores, the following problems occur: airborne germs are stressed by desiccation in the air. Moreover, the media for the detection of the germs are often gamma-sterilized, which again means stress for the medium and therefore leads to poorer growth of the germs to be detected. Both factors lead to the fact that germs of certain kinds, especially gram positive bacteria, and cocci, can no longer be reliably detected in the usual manner (colorimetry with resazurine).

The present invention is therefore addressed to the problem of developing a method by which the growth of bacteria, fungi, yeasts, cocci, can be improved and the detection of the targeted species can be performed reliably and at low cost.

This problem is solved according to the invention by adding to the culture medium sterile-filtered yeast extract and/or p-iodonitrotetrazolium violet.

It was found surprisingly that by the addition of sterile-filtered yeast extract or p-iodonitrotetrazolium violet the growth of bacteria, fungi, yeasts, cocci, can be accelerated. If the redox indicator p-iodonitrotetrazolium violet (INT) is added, the growth of the species under study can be detected simply by colorimetry, while the intensity of calorimetric detection with both additives is synergically increased by the addition of the sterile-filtered yeast extract.

The method of the invention is especially suited to the detection of mycobacteria, and especially clinical *Mycobacterium tuberculosis* isolates which are growing on various media such as 7H9 broth, 7H12, 7H9 with OADC ((oleic acid, albumin, dextrose, catalase, for Trademark, see Difco Manual) and PANTA (polymyxin, amphotericin B, nalidixic acid, trimethoprim, azlocillin) in the MGIT system Mycobacteria Growth Indicator Tube); in Kirchner medium with horse serum, and on solid media such as Löwenstein Jensen.

Even bacteria, especially mycobacteria, damaged by long holding grow better with the additive according to the invention.

The time required for this purpose can be considerably reduced, and detection itself can be simplified.

For example, the sensitivity testing of mycobacteria, which otherwise is possible only within 1 week with the use of a radioactive substrate ($^{14}C$ palmitic acid in Becton Dickinson's Bactex 460 system), can be evaluated even visually within 5 to 7 days by measuring turbidity upon the addition of sterile filtered yeast extract to 7H9 broth, without the need for high-cost systems such as radioactivity detection with the disposal problems which they entail. Furthermore, by the use of a combination with colorimetric substrates, namely INT, the color intensity of the indicator is increased.

The addition made according to the invention is also especially suited for the detection of air-borne germs, because the increase obtained in the germ count by sterile filtered yeast extract results in more rapid growth generally and especially in faster growth than in media that are not gamma-sterilized. Thus the calorimetric detection of germs, especially gram negative bacteria, yeasts and fungi, becomes possible if INT is added as indicator. This also permits the gamma-sterilization of media, and the sterile-filtered yeast extract compensates the damage to the media as regards growth properties. Thus, germs grow on gamma-sterilized media with sterile-filtered yeast extract even slightly better than on conventional, non-gamma sterilized media.

Tryptic soy agar or other such nutrient media can be used as the basic medium.

The addition of sterile-filtered yeast extract according to the invention is performed preferably in liquid form in amounts of 0.5 to 10 g/l, especially 0.5–5 g/l, and 2–2.5 g/l is very especially preferred.

The indicator, iodonitrotetrazolium violet (INT) is added to the culture medium preferably in an amount of 1 to 30 mg/l, especially 5–20 mg/l, and especially 8–15 mg/l.

Furthermore, the growth accelerated according to the invention can be detected calorimetrically in other ways, for example by now adding a small amount of the resazurine/methylene blue system (cf. DE 43 16 394), since the detection of even lower germ counts is possible due to the accelerated growth. This system can be varied in a known manner according to the purpose of the detection; for example, tuberculostatic agents can be added in the sensitivity testing of mycobacteria if growth control is desired. Also, redox stabilizers can be added in this case. The indicators are present in conventional amounts such as 1–200 mg/l and 5–100 mg/l of nutrient medium.

Growth can also be accelerated in other commercial systems by the addition of sterile-filtered yeast extract, as shown in Example 10 below, with Bactec 12B with sterile-filtered yeast extract in comparison with Example 11 (commercial Bactec 12B system), and in accordance with Examples 6, 7 and 8 in MGIT with sterile-filtered yeast extract, and sterile-filtered yeast extract plus INT and INT in comparison with Example 5 in commercial MGIT of Becton Dickinson.

With the addition made according to the invention, it is thus possible in general to accelerate the growth of bacteria, yeasts, cocci and fungi, and in addition to avoid the use of expensive detection apparatus.

The invention will be further explained in the following examples.

I. EXAMPLES 1–12

The growth of *Mycobacterium tuberculosis* was tested on various known media (solid or liquid) in different amounts of inoculant. Media 2, 3, 4, 6, 7, 10 and 12 contain the addition, in accordance with the invention, of sterile-filtered yeast extracts (2, 3, 6, 7, 10, 12) and/or INT (3, 4, 7, 8).

Table I presents the results of this experiment. As it can be seen, a faster growth is achieved with the additive of the invention in specimens 2 and 3 in comparison with 1 (no additive), in specimens 6 and 7 (the invention) in comparison with 9 (comparative example), and in 12 (the invention) in comparison with 11 (comparative example). Furthermore, with the aid of the media containing INT in addition (3 and 7, yeast extract and INT) a more intense coloring is found in comparison with the corresponding media with INT oney (4 and 8).

The first 12 components are autoclaved together, and the rest are added as sterile-filtered, sterile solutions (without autoclaving).

Yeast extract is available commercially. 5 g yeast extract is dissolved in 200 ml dist. water by stirring for 1 hour. The resulting solution is filtered over a prefilter, followed by a sterile-filtration using a 0.2 μm filter as final filter. The prefilter is a Nillex-AP50 prefilter from Nillipore

| | |
|---|---|
| 5. MGIT from Becton Dickinson<br>4 ml 7H9 broth<br>+OADC<br>+PANTA<br>all components from Becton Dickinson | 6. MGIT with sterile-filtered yeast extract in 0.4 ml water<br>4 ml 7H9 broth<br>+OADC<br>+PANTA<br>+10 mg yeast extract sterile-filtered in 0.4 ml water |
| 7. MGIT with sterile-filtered yeast extract and INT<br>4 ml 7H9 broth<br>+OADC<br>+PANTA<br>+10 mg yeast extract sterile-filtered in 0.4 ml water<br>+0.100 ml INT solution<br>(from Sigma, containing 625 mg/L) | 8. MGIT with INT<br>4 ml 7H9 broth<br>+OADC<br>+PANTA<br>+0.100 ml INT solution<br>(from Sigma, containing 625 mg/L) |
| 9. Bactec 12B<br>Becton Dickinson's broth<br>(basing on 7H9)<br>4 ml<br>+PANTA | 10. Bactec 12B<br>Becton Dickinson's broth<br>(basing on 7H9)<br>4 ml<br>+PANTA<br>+10 mg yeast extract sterile-filtered in 0.4 ml $H_2O$ |
| 11. Löwenstein Jensen medium | 12. Löwenstein Jensen medium with sterile-filtered extract |

| I Salt solution | | |
|---|---|---|
| Potassium hydrogen phosphate | 2.4 g | 2.4 g |
| Magnesium sulfate-7 hydrate | 0.24 g | 0.24 g |
| Trimagnesiumdi-citrate-14-hydrate | 0.6 g | 0.6 g |
| L-asparagine mono-hydrate | 3.6 g | 3.6 g |

Media for the Isolation of Mycobacteria (Examples 1 to 12)

| | 1. Kirchner Medium normal | 2. Kirchner Medium with yeast extract | 3. Kirchner Medium with yeast extract and INT | 4. Kirchner Medium with INT |
|---|---|---|---|---|
| Disodiumhydrogenphosphate-12-hydrate | 3.0 g | 3.0 g | 3.0 g | 3.0 g |
| Potassium dihydrogen phosphate | 4.0 g | 4.0 g | 4.0 g | 4.0 g |
| Magnesium sulfate | 0.6 g | 0.6 g | 0.6 g | 0.6 g |
| Sodium citrate | 2.5 g | 2.5 g | 2.5 g | 2.5 g |
| L-Asparagine | 0.1 g | 0.1 g | 0.1 g | 0.1 g |
| Potassium aspartate | 4.0 g | 4.0 g | 4.0 g | 4.0 g |
| D-Alanine | 2.0 g | 2.0 g | 2.0 | 2.0 g |
| Sodium pyruvate | 0.5 g | 0.5 g | 0.5 g | 0.5 g |
| Hemin (dissolved in 1 ml NaOH) | 1.66 mg | 1.66 mg | 1.66 mg | 1.66 mg |
| Ammonium iron(III) sulfate | 50 mg | 50 mg | 50 mg | 50 mg |
| Distilled water | 900 ml | 800 ml | 800 ml | 900 ml |
| Glycerine autoclaved separately | 20 ml | 20 ml | 20 ml | 20 ml |
| Horse serum (inactivated 1 h at 56° C.) | 100 ml | 100 ml | 100 ml | 100 ml |
| Catalase solution (Boehringer Mannheim 106836) | 5 ml | 5 ml | 5 ml | 5 ml |
| Ribonucleic acid solution | 25 μg | 25 μg | 25 μg | 25 μg |
| Yeast extract, sterile-filtered | — | 2.5 g in 100 ml $H_2O$ | 2.5 g in 100 ml $H_2O$ | |
| INT Solution (Sigma 9405), containing 625 mg/L) INT = p-iodonitrotetrazoliumviolet = (2-[-iodophenyl]-3-[4-nitrophenyl-5 phenyltetrazolium chloride | — | — | 24 ml | 24 ml |

-continued

| | | | |
|---|---|---|---|
| glycerine 84–87% solution V/N | 12.0 ml | | 12.0 ml |
| Distilled water | 600 ml | | 350 ml |
| II Malachite Green Solution | | | |
| Malachite green | 2.0 g | | 2.0 g |
| Dist water to make | 100.0 ml | to make | 100. ml |
| III Potato flour emulsion | | | |
| Salt solution from I | 600 ml | | 350 ml |
| Malachite solution from II | 20 ml | | 20 ml |
| Potato flour | 30 g | | 30 g |
| Emulsion sterilized 30 min at 112° C. | | | |
| IV | | | |
| 1000 ml of 20–25 eggs mix homogenized with 620 ml of III | 1000 ml, | mix homogenized with 370 ml of III + 150 ml $H_2O$ containing 4.0 g yeast extract sterile-flitered | 1000. ml |

II. EXAMPLES 13–15

In these examples, sensitivity testing based on the method described in DIN 58942, Part 8, for the detection of mycobacteria was employed in the case of the fluid media 13, 14 and 15 to 15C. The evaluation was performed by the finding of turbidity in the control (and in the case of resistance, also by turbidity) in the case of media 13 and 14. In media 15 to 15C, resistance and growth were evaluated by the occurrence of purple-colored colonies.

Use was made of 7H9 medium with ADC enrichment (standard) and, for the invention, 7H9 medium with ADC enrichment plus sterile-filtered yeast extract, as well as 7H9 medium with ADC enrichment plus sterile-filtered yeast extract plus INT.

DIN 58942, Part 8 is essentially the proportion method as described by Leonid B. Heifets in Drug susceptibility in the Chemotherapy of Nycobacterial Infections, Boca Raton, Fla. (CRC Press) 1991, page 89–121. It is used as one of the standard methods at the National Jewish Hospital in Denver (Colo.) by Mr. Heifets.

TABLE I

Growth of Mycobacterium tuberculosis inoculated in different amounts on the specified media

| Amount of inoculum | Growth on medium No. in days: 1 Std. | 2 Inv | 3 Invention | 4 Invention | 5* Std. | 6* Inv | 7* Invention | 8* Invention | 11 Std | 12 Inv. | 9 Std. | 10 Inv. |
|---|---|---|---|---|---|---|---|---|---|---|---|---|
| M. Tuberculosis H37RV Mcfarland 0.5 x | | | | | | | | | | | | |
| $10^{-2}$ | 7 | 5 | 5 purple | 7 purple | 6 | 5 | 5 purple | 6 purple | 10 | 8 | 5 | 4 |
| $10^{-3}$ | 11 | 8 | 8 purple | 10 purple | 9 | 7 | 7 purple | 8 purple | 14 | 11 | 6 | 5 |
| $10^{-4}$ | 14 | 11 | 11 dark purple | 12 purple | 12 | 10 | 10 dark purple | 11 purple | 18 | 14 | 9 | 7 |
| $10^{-5}$ | 16 | 12 | 12 dark purple | 15 purple | 14 | 12 | 12 dark purple | 13 purple | 22 | 17 | 11 | 10 |
| $10^{-4}$ | 23 | 16 | 15 dark purple | 10 purple | 17 | 14 | 14 dark purple | 15 purple | 28 | 20 | 13 | 12 |
| $10^{-7}$ | 28 | 19 | 19 purple | 24 purple | 20 | 18 | 18 dark purple | 19 purple | 33 | 25 | 17 | 16 |
| Clinical M. Tuberculosis 1 Mcfarland 0.5 x | | | | | | | | | | | | |
| $10^{-2}$ | 9 | 6 | 6 purple | 6 purple | 8 | 6 | 6 purple | 7 purple | 11 | 9 | 5 | 4 |
| $10^{-3}$ | 13 | 9 | 8 purple | 12 purple | 12 | 9 | 9 purple | 11 purple | 15 | 13 | 9 | 7 |
| $10^{-4}$ | 17 | 11 | 10 dark purple | 16 purple | 16 | 12 | 11 dark purple | 16 purple | 20 | 16 | 11 | 10 |
| $10^{-5}$ | 22 | 13 | 13 dark purple | 20 purple | 21 | 14 | 14 dark purple | 20 purple | 25 | 20 | 14 | 12 |
| $10^{-6}$ | 26 | 17 | 16 dark purple | 25 purple | 25 | 18 | 17 dark purple | 25 purple | 30 | 24 | 17 | 15 |
| $10^{-7}$ | 32 | 21 | 20 dark purple | 30 purple | 30 | 20 | 20 dark purple | 29 purple | 36 | 28 | 19 | 18 |
| Clinical M. tuberculosis 15 Mcfarland 0.5 x | | | | | | | | | | | | |
| $10^{-2}$ | 8 | 5 | 5 purple | 8 purple | 6 | 5 | 5 purple | 6 purple | 11 | 9 | 5 | 4 |
| $10^{-3}$ | 12 | 8 | 8 purple | 12 purple | 9 | 8 | 8 purple | 9 purple | 14 | 12 | 7 | 6 |
| $10^{-4}$ | 15 | 11 | 11 dark purple | 15 purple | 12 | 11 | 11 dark purple | 12 purple | 18 | 14 | 10 | 9 |
| $10^{-5}$ | 22 | 13 | 13 dark purple | 21 purple | 14 | 12 | 12 dark purple | 14 purple | 25 | 19 | 12 | 11 |
| $10^{-6}$ | 26 | 17 | 16 dark purple | 25 purple | 18 | 16 | 15 dark purple | 17 purple | 30 | 23 | 15 | 14 |
| $10^{-7}$ | 29 | 20 | 19 dark purple | 29 purple | 22 | 19 | 18 dark purple | 20 purple | 35 | 27 | 18 | 16 |

*In 5 and 6, evaluation by fluorescence in accordance with instructions on MGIT
In 7 and 8, evaluation by fluorescence in accordance with instructions on MGIT and additional occurence of purple colonies (due to INT)

| 13 | 14 | 15 |
|---|---|---|
| 13 Middlebrook 7H9 broth 4,7 g/l autoclaved<br><br>+ADC enrichmnent 100 ml to 900 ml 7H9 base medium (per instructions of the medium manufacturer, Difco)<br><br>(Standard) | 14 with addition of sterile-filtered yeast extract<br><br>Middlebrook 7H9 broth 4.7 g/l autoclaved<br>800 ml 7H9 base medium<br>100 ml ADC enrichment<br>100 ml $H_2O$, containing 2.5 g sterile-filtered yeast extract<br><br>(The invention) | 15 with addition of sterile-filtered yeast extract and INT<br>Middlebrook 7H9 broth 4.7 g/l autoclaved<br>800 ml 7H9 base medium<br>100 ml ADC enrichment<br>100 ml $H_2O$ containing 1.5 g sterile-filtered yeast extract<br>24 ml INT solution<br>15A differing from 15 as follows: 100 ml $H_2O$ containing 3.0 g sterile-filtered yeast extract.<br>15B differing from 15 as follows: 100 ml $H_2O$ containing 2.0 g sterile-filtered yeast extract;<br>15C differing from 15 as follows: 100 ml $H_2O$ containing 0.5 sterile-filtered yeast extract<br>(The invention) |

The results are reflected in the following Table II.

TABLE II

| Strain | Antituberculo-static | MIC* in µg/ml | Readable MIC after days in Medium 13 std. | 14 inv. | 15 inv. | 15A | 15B | 15C |
|---|---|---|---|---|---|---|---|---|
| M.tb. $H_{37}$ $R_v$ | Rifampicin (RMP) | 2.0 | 9 | 5 | 5 | 5 | 5 | 6 |
| Clin. M.tb 1 | Rifampicin (RMP) | 1.0 | 11 | 7 | 7 | 7 | 7 | 8 |
| Clin. M.tb 15 | Rifampicin (RMP) | 2.0 | 9 | 5 | 5 | 5 | 5 | 6 |
| M.tb. $H_{37}$ $R_v$ | Isoniacid (INA) | 0.06 | 9 | 5 | 5 | 5 | 5 | 6 |
| Clin. M.tb 1 | Isoniacid (INA) | 0.03 | 11 | 7 | 7 | 7 | 7 | 8 |
| Clin. M.tb 15 | Isoniacid (INA) | 0.03 | 9 | 5 | 5 | 5 | 5 | 6 |
| M.tb. $H_{37}$ $R_v$ | Ethambutol (EMB) | 0.5 | 9 | 5 | 5 | 5 | 5 | 6 |
| Clin. M.tb 1 | Ethambutol (EMB) | 0.25 | 11 | 7 | 7 | 7 | 7 | 8 |
| Clin. M.tb 15 | Ethambutol (EMB) | 0.5 | 9 | 5 | 5 | 5 | 5 | 6 |

*MIC = minimum inhibiting concentration

As it is apparent from the above, specimens 14 and 15 are evaluated more rapidly with the additive according to the invention than in the standard medium 13.

Moreover, calorimetric detection is possible with the addition of INT in media 15 to 15C. Examples 15A–15C show different amounts of yeast extract added.

III. EXAMPLES 16–18

In the following Examples 16–18 are listed media with (Examples 17, 18) and without (Example 16) the additive according to the invention, which were used with (16A, 17A) and without (16, 17, 18) previous gamma sterilization (gamma rays of 20–30 Kilogray) as growth media for different airborne germs listed in Table III.

| 16 | 17 |
|---|---|
| 16. Tryptic soy agar for germ counting. | 17. Tryptic soy agar for germ counting, with sterile-filtered yeast extract |
| | 15 g |
| 15 g Pancreatic digest of casein | 5 g |
| 5 g soybean peptone | 5 g |
| 5 g NaCl | 0.7 g |
| 0.7 g lecithin | 7 g |
| 7 g polysorbate 80 | 17 g |
| 17 g agar | 900 ml $H_2O$ |
| 1000 ml $H_2O$ | The mixture is autoclaved |
| The mixture is autoclaved | Add 100 ml sterile $H_2O$ containing 2.5 g of sterile-filtered yeast extract |
| 18. Tryptic soy agar for germ counting with sterile-filtered yeast extract and INT<br>15 g pancreatic digest of casein<br>5 g soy bean peptone<br>5 g NaCl<br>0.7 g lecithin<br>7 g polysorbate 80<br>17 g agar<br>900 ml $H_2O$<br>The mixture is autoclaved<br>Add 100 ml sterile $H_2O$ containing 2.5 g sterile-filtered yeast extract. | |

As it is apparent from Table III, medium 17 (inv.) shows a substantial improvement in the number of re-found colonies over 16 (std.)

It can also be seen that the number of re-found colonies diminishes due to the stress of the gamma radiation (media 16A, 17A) as compared with the non-irradiated media (16, 17).

If 17A (sterile-filtered, plus additive according to the invention) is compared with 16 (standard), it is seen that a gamma-irradiated medium which still contains sterile-filtered yeast extract still provides at least the same, but sometimes better results than a non-irradiated normal medium.

TABLE III

| Strain and amount inoculate | Growth on medium No., and number of colonies after 1 day 16 | 16A | 17 | 17A | 18 |
|---|---|---|---|---|---|
| | | | *Bacillus subtilis* | | |
| $10^3$ | 80 | 11 | profuse | 95 | 58 purple colonies |
| $2 \times 10^2$ | 10 | 1 | 52 | 20 | 0 purple colonies |
| 50 | 1 | 0 | 16 | 4 | 0 purple colonies |
| | | | *Staph. aureus* ATCC 6538 | | |
| $10^3$ | profuse | 68 | profuse | profuse | 116 purple colonies |
| $2 \times 10^2$ | 138 | 27 | profuse | 119 | 2 purple colonies |
| 50 | 32 | 1 | 68 | 35 | 0 purple colonies |
| | | | *Candida pseudotropicalis* | | |
| $10^3$ | 17 | 2 | 52 | 21 | 48 purple colonies |
| $2 \times 10^2$ | 3 | 0 | 12 | 11 | 10 purple colonies |
| 50 | 1 | 0 | 3 | 4 | 3 purple colonies |
| | | | *Alteromonas putrefaciens* | | |
| $10^3$ | profuse | 59 | profuse | profuse | profuse purple |
| $2 \times 10^2$ | 66 | 21 | 139 | 78 | 128 purple colonies |
| 50 | 11 | 2 | 51 | 24 | 48 purple colonies |

IV. CLINICAL EXPERIMENTS

With a different nutrient medium and a medium containing the addition according to the invention of sterile-filtered yeast extract and INT, clinical experiments were conducted with various specimen materials for the detection of *mycobacterium tuberculosum.*

The results are given in Table IV below.

TABLE IV

| Specimen material | Medium 3 in accord with the invention | Bectec 12B (standard) | Löwenstein Jensen (standard) | Conventional Kirchner media (standard) |
|---|---|---|---|---|
| Sputum* | positive after 18 days | negative | negative | negative |
| Sputum | positive after 18 days | positive after 18 days** | positive after 28 days | positive after 21 days |
| Sputum | positive after 15 days | positive after 15 days** | positive after 21 days | positive after 18 days |
| Fluid from lung tap | positive after 18 days | negative | negative | negative |
| Bronchial washing | positive after 20 days | negative | negative | negative |
| Sputum | positive after 16 days | negative | negative | negative |

*Treated patients, Tb diagnosis confirmed by preliminary tests
**In the medium according to the invention the differentiation of the species with commercial DNA probes of gene specimen can be performed immediately. In the case of Bectec 12B another 3–4 days are required in order to achieve a growth index of 500 so as to be able to use these probes reliably.

Table IV shows that germs damaged and stressed by previous treatment can still be cultured in the medium according to the invention, whereas this is no longer the case in the media with which it is compared.

Furthermore, immediate processing with molecular-biological DNA probes is possible with the medium according to the invention on the same day on which the positive finding of growth is made. Consequently differentiation of species and an immediate finding is possible at the clinics, whereas in traditional systems it is necessary to wait longer in order to have sufficient germs for testing with commercial DNA probes.

As it is dearly apparent from these examples, the method of the invention leads to fast, reliable results as regards the growth and detection of many different species.

What is claimed is:

1. A method for accelerating a growth of bacteria or fungi in culture, said method comprising the following steps:

a) adding to a culture medium one member but not both members selected from the group consisting of i) yeast extract which has been sterile filtered without autoclaving and ii) p-iodonitrotetrazoliumn violet; and b) growing and detecting bacteria or fungi in said culture medium;

wherein the growth of said bacteria or fungi is accelerated as compared to the growth of bacteria or fungi of the same species which have not been subjected to said adding.

2. The method according to claim 1, wherein said bacteria are cocci and said fungi are yeasts.

3. The method according to claim 1, which is for growing and detecting mycobacteria.

4. The method according to claim 3, which is for growing and detecting strains of *Mycobacterium tuberculosis.*

5. The method according to claim 1, which is for growing and detecting bacteria or fungi under stress conditions.

6. The method according to claim 1, wherein said culture medium is selected from the group consisting of:

a) liquid media optionally comprising oleic acid, albumin, dextrose, catalase, polymyxin, amphotericin B, nalidixic acid, trimethoprim and azlocillin or optionally comprising horse extract;

b) solid media based on egg or egg jelly; and c) tryptic soy agar.

7. The method according to claim 1, which comprises using a resazurine/methylene blue indicator system as an indicator.

8. A method for accelerating a growth of bacteria or fungi in culture, said method comprising the following steps:

a) adding to a culture medium yeast extract which has been sterile filtered without autoclaving; and b) growing and detecting bacteria or fungi in said culture medium;

wherein the growth of said bacteria or fungi is accelerated as compared to the growth of bacteria or fungi of the same species which have not been subjected to said adding.

9. The method according to claim 8, which comprises adding 0.5 to 10 g/l of said yeast extract which has been sterile filtered without autoclaving to said culture medium.

10. A method for accelerating a growth of bacteria or fungi in culture, said method comprising the following steps:

a) adding to a culture medium p-iodonitrotetrazoliumn violet; and b) growing and detecting bacteria or fungi in said culture medium;

wherein the growth of said bacteria or fungi is accelerated as compared to the growth of bacteria or fungi of the same species which have not been subjected to said adding.

11. The method according to claim 10, which comprises adding 1 to 30 mg/l of p-iodonitrotetrazoliur violet to said culture medium.

* * * * *

UNITED STATES PATENT AND TRADEMARK OFFICE

CERTIFICATE OF CORRECTION

PATENT NO. : 6,617,126 B1
DATED : September 9, 2003
INVENTOR(S) : Jürgen Horn

It is certified that error appears in the above-identified patent and that said Letters Patent is hereby corrected as shown below:

Colujmn 12,
Line 5, "p-iodonitrotetrazoliur" should read -- p-iodonitrotetrazlium --.

Signed and Sealed this

Seventeenth Day of August, 2004

JON W. DUDAS
*Acting Director of the United States Patent and Trademark Office*